(12) United States Patent
Ohishi

(10) Patent No.: US 7,844,029 B2
(45) Date of Patent: Nov. 30, 2010

(54) X-RAY DIAGNOSTIC APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/608,668

(22) Filed: Oct. 29, 2009

(65) Prior Publication Data

US 2010/0046710 A1 Feb. 25, 2010

Related U.S. Application Data

(63) Continuation of application No. 12/056,700, filed on Mar. 27, 2008, now Pat. No. 7,706,504.

(30) Foreign Application Priority Data

Mar. 30, 2007 (JP) ............................. 2007-094689

(51) Int. Cl.
H05G 1/10 (2006.01)

(52) U.S. Cl. ...................................................... 378/95

(58) Field of Classification Search ............... 378/4–20, 378/62, 95
See application file for complete search history.

(56) References Cited

U.S. PATENT DOCUMENTS 7,379,532 B2 5/2008 Kramp .................. 365/189.07
2003/0069499 A1 4/2003 Lienard et al. .............. 600/431

FOREIGN PATENT DOCUMENTS

CN 2151483 Y 12/1993
CN 1927123 A 3/2007

*Primary Examiner*—Courtney Thomas
(74) *Attorney, Agent, or Firm*—Oblon, Spivak, McClelland, Maier & Neustadt, L.L.P.

(57) ABSTRACT

An X-ray diagnostic apparatus includes an X-ray generating unit which generates X rays, an X-ray detecting unit which detects X rays transmitted through a subject, an X-ray exposure operating unit which is operated by an operator, and a system control unit which controls the X-ray generating unit in order to start the generation of the X rays from the X-ray generating unit at a time point when a heart rate phase of the subject reaches a specified phase after the X-ray exposure operating unit is operated.

5 Claims, 6 Drawing Sheets

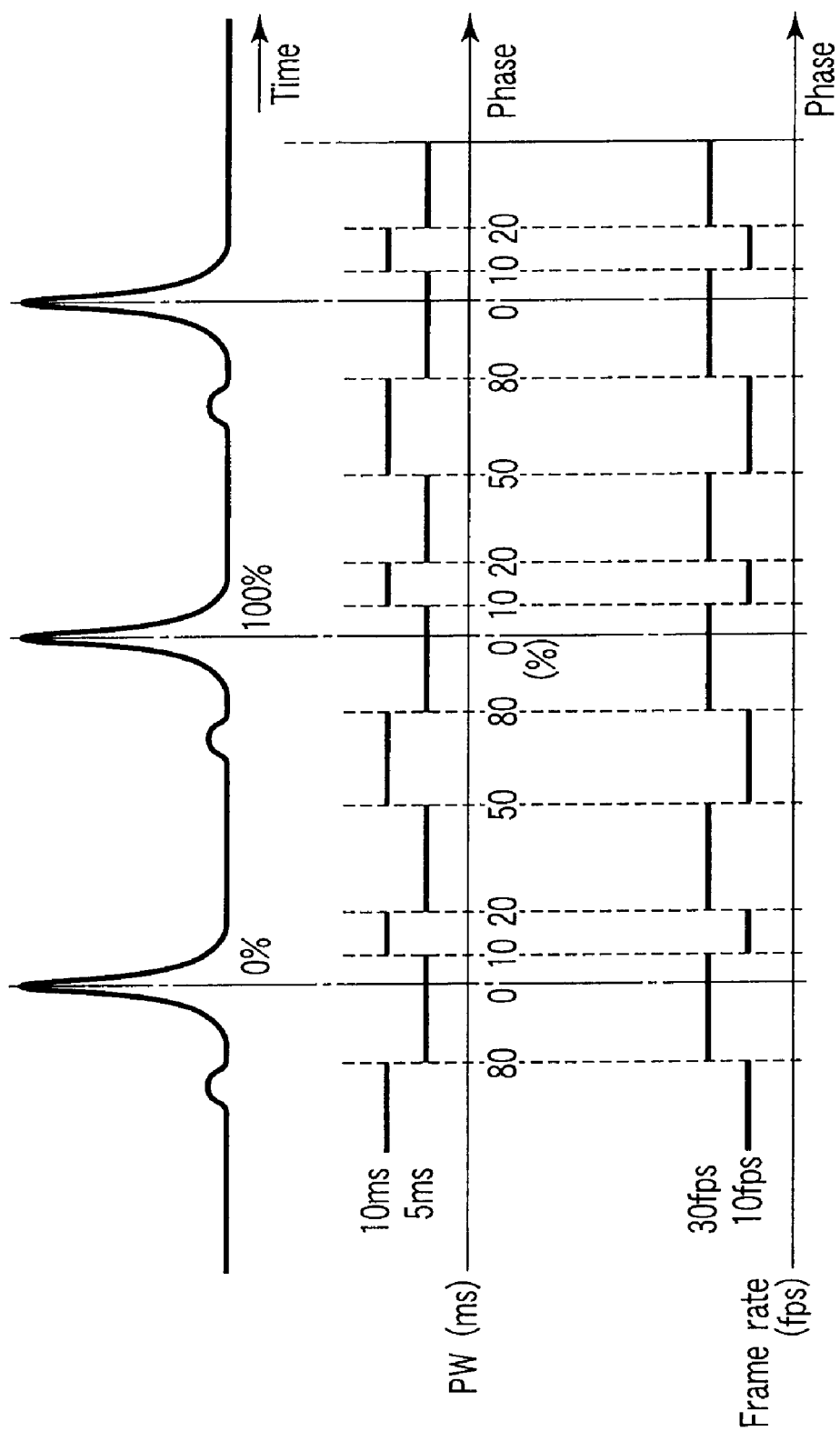
F I G. 10

X-RAY DIAGNOSTIC APPARATUS

CROSS-REFERENCE TO RELATED APPLICATIONS

This application is a continuation application of U.S. patent application Ser. No. 12/056,700, filed Mar. 27, 2008, which is based upon and claims the benefit of priority from prior Japanese Patent Application No. 2007-094689, filed Mar. 30, 2007. The entire contents of the above applications are incorporated herein by reference.

BACKGROUND OF THE INVENTION

1. Field of the Invention

The present invention relates to an X-ray diagnostic apparatus which copes with contrast study of a heart or the like.

2. Description of the Related Art

In X-ray contrast study of hearts and intervention, it is very important to understand shapes and functions of blood vessels and hearts. However, since cardiac movement cannot be avoided differently from the other regions of bodies, projection data is mainly used for the understanding of the hearts.

In recent years, applications for heart regions are gradually being developed. They include an application for creating a digital subtraction angio (DSA) image of coronary artery, an application for identifying perfusion from coronary artery to cardiac muscle, an application for locally/wholly creating a three-dimensional structure of coronary artery, and the like.

In order to create a DSA image of coronary artery, an image which hardly has an effect of a contrast agent is required as a satisfactory mask image for at least one heart rate. In some cases, the timing at which injection of contrast agent starts is too early and thus satisfactory mask images for one heart rate cannot be collected. This becomes a fatal problem for the creation of DSA images. Also when the perfusion from coronary artery to cardiac muscle is identified, the similar problem might arises.

When a three-dimensional structure of coronary artery is locally or wholly created, an image at end-diastole with comparatively less movement becomes a key. For example, in a method for paying an attention only to a target region and correcting a movement of this region so as to create a local three-dimensional structure, a target region is specified on an image at end-diastole.

When photographing is started just after the end-diastole passes, the number of end-diastoles to be included in an any photographing zone might be reduced. Since the amount of specifying information is reduced in this case, information is insufficient, and thus restructure is at risk of being unsatisfactory.

On the other hand, when a three-dimensional structure of coronary artery is wholly created, the restructure is carried out by using only images at end-diastole and less information. In such a method, image quality is greatly influenced by whether the number of end-diastoles is reduced by one or increased by one.

BRIEF SUMMARY OF THE INVENTION

It is an object of the present invention to collect necessary images of heart rate phase by means of less radiation dose.

According to a first aspect of the present invention, there is provided an X-ray diagnostic apparatus comprising: an X-ray generating unit which generates X rays; an X-ray detecting unit which detects X rays transmitted through a subject; an X-ray exposure operating unit which is operated by an operator; and a control unit which controls the X-ray generating unit so as to start the generation of the X rays from the X-ray generating unit at a time point when a heart rate phase of the subject reaches a specified phase after the X-ray exposure operating unit is operated.

According to a second aspect of the present invention, there is provided an X-ray diagnostic apparatus, comprising: an X-ray generating unit which generates X rays; an X-ray detecting unit which detects the X rays transmitted through a subject; and a control unit which controls the X-ray generating unit in order to change a pulse width of the X rays according to heart rates of the subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a diagram illustrate a state that the pulse width is changed dynamically according to the heart rate phase in the embodiment.

DETAILED DESCRIPTION OF THE INVENTION

An embodiment of the present invention will be described below with reference to the drawings.

In an outline of the embodiment, conventionally photographing is started at the moment when a photographing start trigger is turned on, but in this embodiment, moreover, photographing is started at the moment when a heart rate phase reaches a predetermined heart rate phase or before a constant time from the scheduled time point. As a result, necessary images of the heart rate phase are collected without excess and deficiency. The start of contrast is specified after at least one cycle passes from the start of photographing. As a result, necessary information (mask images at necessary cycles) can be collected securely.

Figure 1:
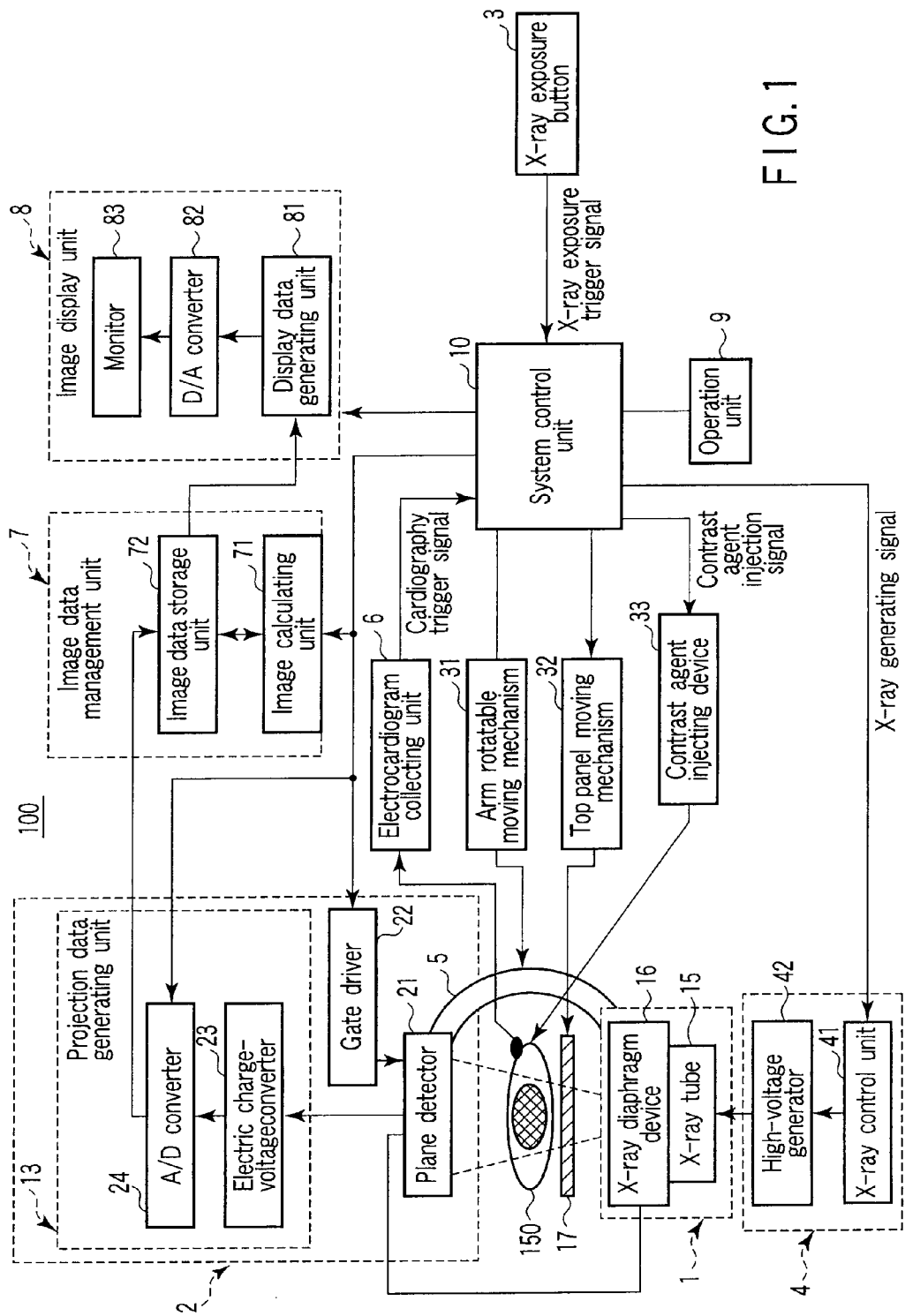
FIG. 1 is a diagram illustrating a structure of an X-ray diagnostic apparatus according to an embodiment of the present invention.

FIG. 1 illustrates a structure of the X-ray diagnostic apparatus of the embodiment. The X-ray diagnostic apparatus 100 in the embodiment has an X-ray generating unit 1 which generates X rays for irradiating a subject 150. The X-ray generating unit 1 has an X-ray tube 15 which generates X rays, and an X-ray diaphragm device 16 which forms a radiation field of X rays. A high-voltage generator 42 of a high-voltage generating unit 4 applies a high voltage to the X-ray tube 15 under the control of an X-ray control unit 41, and supplies a filament current. As a result, X rays are generated from the X-ray tube 15. The X-ray tube 15 is supported a C-shaped arm 5 which is supported rotatably to an arm rotatable moving mechanism 31 on at least three orthogonal shafts. A plane detector 21 of an X-ray detecting unit 2 is held to a position and direction on the C-shaped arm 5 opposed to the X-ray tube 15.

The plane detector 21 has a plurality of semiconductor detecting elements arrayed two-dimensionally, for example. X rays, which transmit through the subject 150 placed on a top panel 17 supported movably to a top panel moving mechanism 32 of a bed, are converted into electric charges by the plurality of semiconductor detecting elements of the plane detector 21 so that the electric charges are accumulated. The accumulated electric charges are read as a current signal for each semiconductor detecting element or each channel by gate driving of a gate driver 22. An electric charge-voltage converter 23 of a projection data generating unit 13 converts the current signals read from the plane detector 21 into voltage signals for each semiconductor detecting element or each channel. An analog-digital (A/D) converter 24 converts the voltage signal converted by the electric charge-voltage converter 23 into a digital signal for each semiconductor detecting element or each channel, so as to output it as image data. An image data storage unit 72 of an image data management unit 7 stores image data calculated by raw image data or an image calculating unit 71. An image display unit 8 has a display data generating unit 81, a digital-analog (D/A) converter 82 and a monitor 83 in order to display image data read from the image data storage unit 72.

An electrocardiogram collecting unit 6 is attached to the subject 150 placed on the top panel 17. The electrocardiogram collecting unit 6 has a function for measuring an electrocardiogram of the subject 150, and a function for detecting a specified heart rate phase desired by a doctor based on the electrocardiography waveform so as to repeatedly generate a pulse-shaped cardiography trigger signal. The specified heart rate phase may be specified by a doctor or the like on free setting or may be automatically set as a default value for each photographing program and each photographing mode (analysis type).

The heart rate phase is expressed in such a manner that a period from an R wave to a next R wave is standardized according to percentage and the position of the period is expressed by percentage. For example, when a three-dimensional structure of coronary artery is created locally or wholly, the heart rate phase corresponding to end-diastole with less movement is set as the "specified heart rate phase". For convenience of description, a cardiography trigger signal is generated when the specified heart rate phase is 0%, namely, at the timing of an R wave.

A contrast agent injecting device 33 is attached to the subject 150 placed on the top panel 17. The contrast agent injecting device 33 is called an injector which automatically injects a constant agent to the subject 150 at timing, injecting amount and an injecting speed which are controlled by a contract agent injection signal from the system control unit 10.

An X-ray exposure button 3 as well as a general operating unit 9 for inputting photographing conditions and the like is connected to the system control unit 10. The X-ray exposure button 3 is typically a push button, and while an operator is pressing down the button, an X-ray exposure trigger signal is generated continuously.

Figure 2:
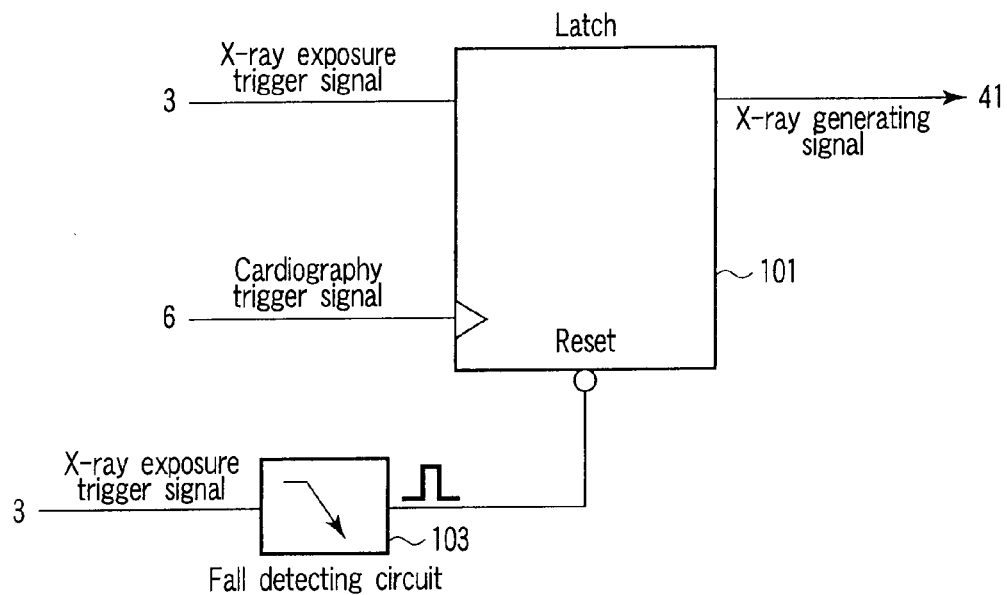
FIG. 2 is a diagram illustrating a structure relating to a generation portion of an X-ray generation signal in a system control unit of FIG. 1.

As shown in FIG. 2, an X-ray signal generating unit 101, which is constituted as, for example, a latch circuit in the system control unit 10, substantially generates an X-ray generation signal for a X-ray control unit 4 continuously for a specified period based on an X-ray exposure trigger signal supplied from the X-ray exposure button 3 and a cartographic trigger signal supplied from the electrocardiogram collecting unit 6. A fall detecting circuit 103 is connected to the X-ray signal generating unit 101. The fall detecting circuit 103 detects fall of an X-ray exposure trigger signal corresponding to release of a pushing-down operation of the X-ray exposure button 3. When the fall detecting circuit 103 detects fall of the X-ray exposure trigger signal or the fall detecting circuit 103 inputs a signal expressing the detection of the fall of the X-ray exposure trigger signal, the X-ray signal generating unit 101 suspends an X-ray generation signal.

While receiving the X-ray generation signal from the system control unit 10, the X-ray control unit 4 continuously supplies a filament current to the X-ray tube 15 from the high-voltage generator 42, and generates a control signal for repeatedly applying a pulse-shaped X-ray tube voltage. The system control unit 10 generates a control signal for allowing the gate driver 22 to execute an electric charge reading operation in synchronization with an X-ray generation signal, and generates a control signal for allowing the analog-digital converter 24 to execute an analog-digital converting operation. With the control signals, the X-ray photographing is repeated in a constant cycle during a specified period for which the X-ray generation signal is generated, and data about a series of a plurality of images are generated.

The system control unit 10 generates a contrast agent injection signal for the contrast agent injecting device 33 continuously for a period different from the X-ray generation signal generating period based on the X-ray exposure trigger signal supplied from the X-ray exposure button 3 and the cardiography trigger signal supplied from the electrocardiogram collecting unit 6. The contrast agent injecting device 33 continuously injects a contrast agent into the subject 150 while receiving the contrast agent injection signal from the system control unit 10.

Figure 3:
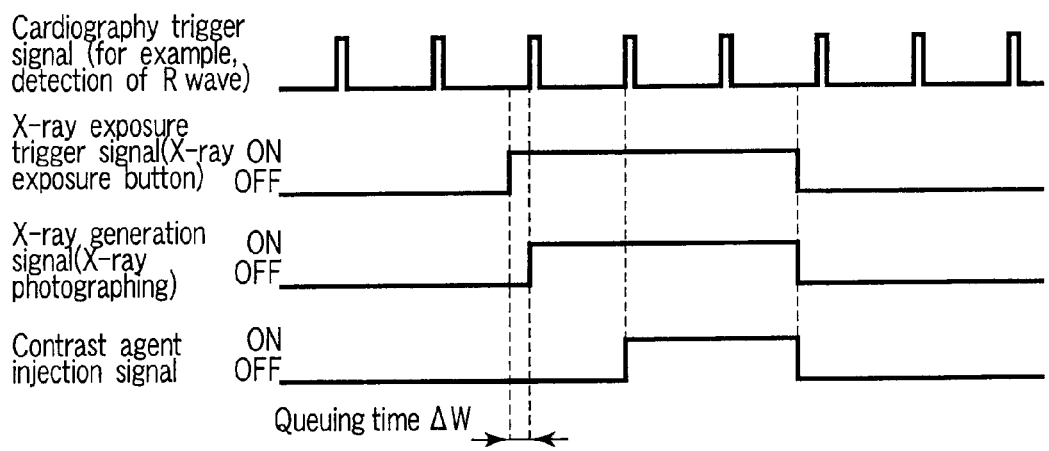
FIG. 3 is a diagram illustrating timing of the X-ray generation signal and a contrast agent injection signal in the embodiment.

FIG. 3 illustrates a time chart relating to the X-ray exposure operation and the contrast agent injecting operation by means of the system control unit 10. The cardiography trigger signal which is typically synchronous with the R wave is supplied from the electrocardiogram collecting unit 6 to the system control unit 10 at a stage of an off state before pushing-down of the X-ray exposure button 3 (on state). In this state, the system control unit 10 waits for the supply of the X-ray exposure trigger signal from the X-ray exposure button 3. The supply of the X-ray exposure trigger signal is equivalent to a change of the X-ray exposure trigger signal from a standard voltage into a specified voltage. For convenience of description, the supply/suspend of the X-ray exposure trigger signal is described here. Much the same is true on the X-ray generation signal. The X-ray exposure trigger signal is supplied to the system control unit 10 continuously during a period for which the X-ray exposure button 3 is being pushed down, and the supply of the X-ray trigger signal to the system control unit 10 is suspended during a period for which the X-ray exposure button 3 is released.

The system control unit 10 does not generate an X-ray generation signal immediately at the time point when the X-ray exposure button 3 is pushed down and the X-ray exposure trigger signal is supplied, but receives the X-ray exposure trigger signal and then stands by until the first cardiography trigger signal is supplied (queuing time ΔW), so as to generate the x-ray generation signal. The queuing time ΔW is not prescribed time but fluctuation time according to a period up to a first R wave after the X-ray exposure button 3 is pushed down. As described, The X-ray generation signal is generated at the time point of the first R wave after the X-ray exposure button 3 is pushed down. Therefore, even when image data for the period up to the time point of the first R wave after the X-ray exposure button 3 is pushed down is not necessary for diagnosis, such useless photographing can be avoided.

Figure 4:
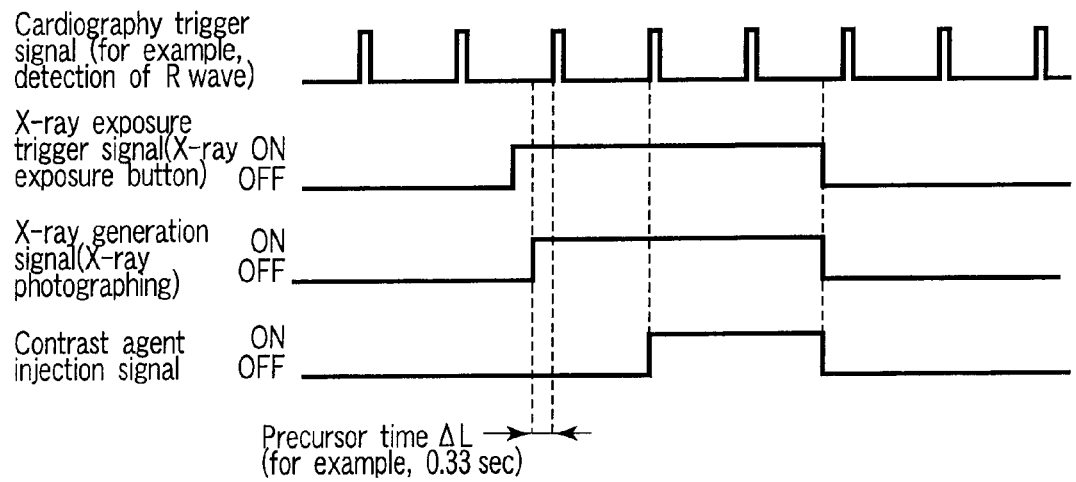
FIG. 4 is a diagram illustrating another timing of the X-ray generation signal and the contrast agent injection signal in the embodiment.

As shown in FIG. 4, a certain margin is given to a predetermined heart rate phase, and the photographing may be started slightly earlier by specified precursor time ΔL than the time point of the first R wave after the pushing-down of the X-ray exposure button 3, actually, the estimation time point when a R wave whose average cycle passes from a previous R wave is generated. In this case, the cardiography trigger signal is not a specified phase, but is brought into an on state at the time earlier by the precursor time ΔL. The precursor time ΔL may be designed based on time until blur of the heart rate cycle and collected image luminance become stable and time until the rotation at the time of rotational photographing becomes stable, and is set to 0.33 second, for example.

The system control unit 10 generates the X-ray exposure trigger signal continuously while a device operator is pushing down the X-ray exposure button 3, and when the device operator releases the X-ray exposure button 3, namely, at the time point when the device operator releases the X-ray exposure button 3 regardless of the heart rate phase differently from the start of photographing, the X-ray exposure trigger signal is suspended instantly. As a result, the X-ray exposure is suspended immediately, and the photographing is ended.

The injection of the contrast agent is required for a contrast study such as DSA of coronary artery. The X-ray exposure button 3 is pushed down and the X-ray exposure trigger signal is supplied, and then at the time when a preset second or n-th (n: integer of not less than 3) cartography trigger signal is supplied, the system control unit 10 generates the contrast agent injection signal. As a result, the injection of the contrast agent from the contrast agent injecting device 33 to the subject 150 is started. That is, at the time point of the second or n-th R wave after the device operator pushes down the X-ray exposure button 3, the injection of the contrast agent is started. Therefore, the photographing is started at the time point of the first R wave after the device operator pushes down the X-ray exposure button 3, and then the injection of the contrast agent is started with being delayed by at least one heart rate period. For this reason, at least one heart rate period can be secured as a photographing period of a mask image with few influence of the contrast agent. The heart rate phase where the injection of the contrast agent starts is described as the "specified heart rate phase", namely, the same phase as that of the photographing start, but another heart rate phase different from the "specified heart rate phase" corresponding to the photographing start may be set.

The contrast agent may be injected manually instead of using the contrast agent injecting device 33. In this case, a message that the contrast agent should be injected, for example, is displayed on the screen of a display device according to the contrast agent injection signal. Also in this case, at the time point of the second or n-th R wave after the device operator pushes down the X-ray exposure button 3, the device operator is urged to start the injection of the contrast agent. Therefore, the photographing is started at the time point of the first R wave after the device operator pushes down the X-ray exposure button 3, and then the device operator is urged to start the injection of the contrast agent by the message with being delayed by at least one heart rate period.

Figure 7:
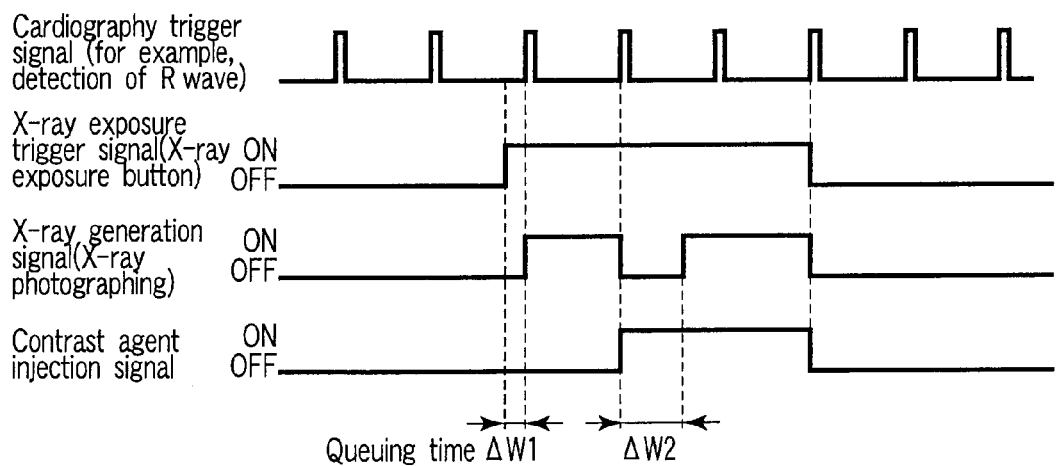
FIG. 7 is a diagram illustrating another timing of the X-ray generation signal and the contrast agent injection signal in the embodiment.

As shown in FIG. 7, the X-ray signal generation signal is off for a predetermined period ΔW2 after which the contrast agent injection signal is on and the first R wave is generated, and thus the generation of X rays is suspended. This period is before the contrast agent reaches a photographing region after it is injected. Applications of images photographed for this period are not much present. When the generation of X rays is suspended for this period, the exposure with X rays can be reduced.

When the X-ray generation signal is on, the system control unit 10 counts the number of heart rate cycles after the X-ray generation signal is on by counting the number of the cartography trigger signals. When the counted value reaches a predetermined number of times, the system control unit 10 does not start the automatic injection of the contrast agent, but may display an injection icon in image display unit for urging the manual injection of the contrast agent. This icon may be a message. As to the counting of the number of heart rate cycles, a zone from R wave to R wave is measured as one cycle, and a zone from the collection starting to the first R wave is calculated by a ratio of the time up to R wave to the one heart rate time. When a difference between the predetermined number of times and the number of cycles measured up to R wave is not more than 1, the number of heart rate cycles is measured by the ratio of the measured number of cycles up to R wave to the one heart rate time. The one heart rate time at this time may be calculated by using current heart rate time, or using maximum heart rate time obtained by multiplying the heart rate time by a constant ratio in order to take a certain margin into consideration. A certain delay time is set for the predetermined number of heart rate times, and the icon may be displayed at timing which is delayed from the predetermined number of heart rates. This margin can absorb the blur of the heart rate cycle.

As seen, it is structured such that unless the X-ray exposure trigger signal and the cartography trigger signal are simultaneously in the on state, the X-ray generation signal is not in the on state. The X-ray exposure trigger signal is in the on state only while the X-ray exposure button 3 is being pushed down. The cartography trigger signal is a signal from the electrocardiogram collecting unit 6, and is generated only at the time of a predetermined heart rate phase. With such a comparatively simple structure, excess or deficiency of the photographing in various photographing methods can be effectively reduced.

Figure 5:
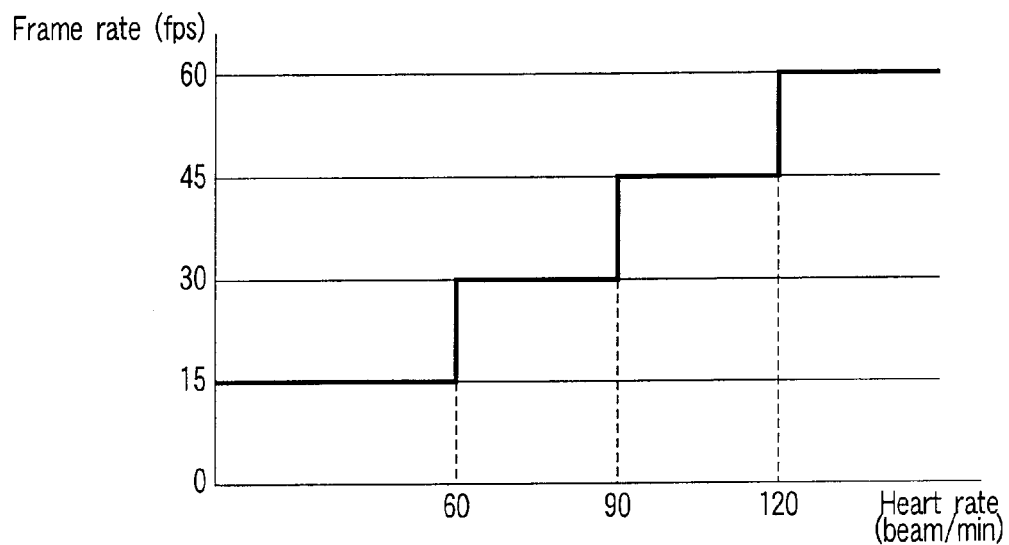
FIG. 5 is a diagram illustrating a change in a frame rate with respect to a change in heart rate by means of control using the system control unit in FIG. 1.

A frame rate during the photographing is described below. As illustrated in FIG. 5, the frame rate representing the number of photographed images per second (fps) is dynamically changed according to a fluctuation in the heart rate by the control of the system control unit 10. The frame rate is adjusted by control signals from the system control unit 10 to the gate driver 22 and A/D converter 24, for example, modulation of a clock signal.

When the heart rate (inverse number of the heart rate cycle) increases, the frame rate is increased gradually, and when the heart rate is reduced, the frame rate is reduced gradually. For example, when the heart rate is not more than 60, the frame rate is set to 15, and when the heart rate is over 60 to not more than 90, the frame rate is set to 30. When the heart rate is over 90 to not more than 120, the frame rate is set to 45, and when the heart rate is over 120, the frame rate is set to 60.

Figure 6:
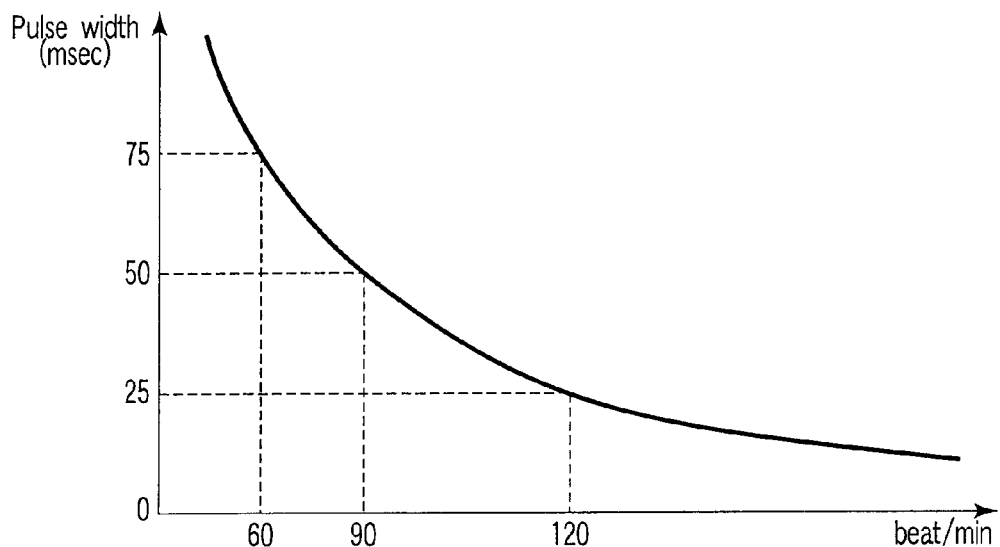
FIG. 6 is a diagram illustrating a change in an X-ray pulse width with respect to the change in the heart rate by means of control using the system control unit in FIG. 1.

A pulse width of X rays during the photographing is described. As shown in FIG. 6, the pulse width of an X-ray pulse is dynamically changed according to the heart rate by the control of the system control unit 10. When the heart rate increases, the pulse width is shortened, and when the heart rate reduces, the pulse width is lengthened. For example, when the heart rate is 60, the pulse width is set to 75 msec, and when the heart rate increases to 90, the pulse width is shortened to 50 msec. When the heart rate is 120, the pulse width is set to 25 msec.

Figure 8:
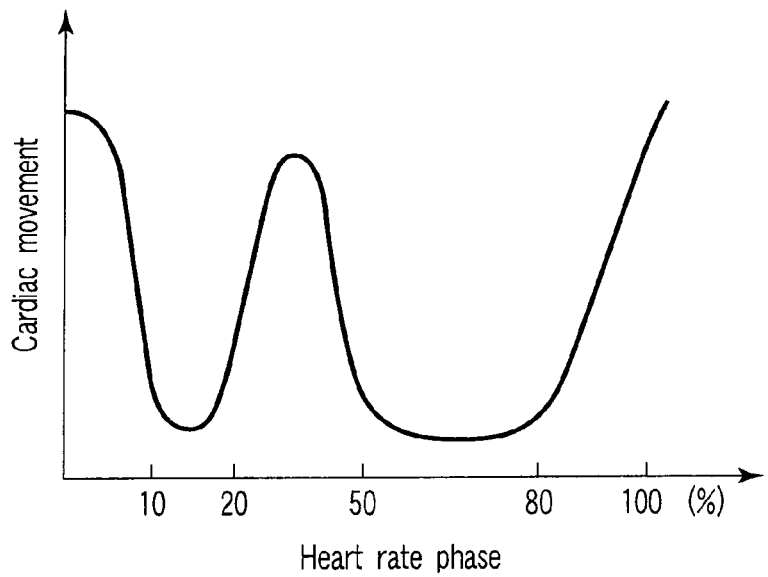
FIG. 8 is a diagram illustrating a relationship between a heart rate phase and a cardiac movement.
Figure 9:
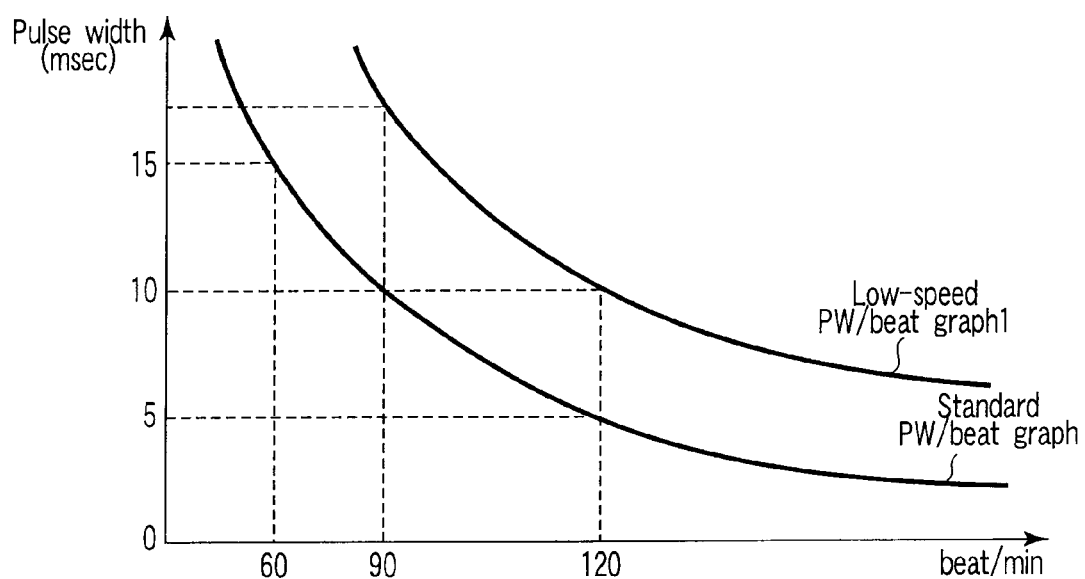
FIG. 9 is a diagram illustrating a pulse width for low-speed-heart rate graph in the embodiment.

The pulse width of X rays may be dynamically changed according to the heart rate phase. As shown in FIG. 8, a cardiac movement, for example a distance between two points on a cardiac muscle surface is changed according to the heart rate phase. As shown in FIG. 9, the system control unit 10 holds a pulse width-heart rate flag related to low speed as well as a standard pulse width-heart rate graph. A standard pulse width is determined according to the heart rate by using the standard pulse width-heart rate graph. The system control unit 10 determines the pulse width for low-speed according to the heart rate using the pulse width for low-speed-heart rate graph. As shown in FIG. 10, the system control unit 10 alternates the standard pulse width and the pulse width for low-speed according to the heart rate phase. When the heart rate phase is included in predetermined (multiple) phase periods, the pulse width of X rays is switched from the standard pulse width into the pulse width for low-speed. For example, for the period for which the heart rate phase is 10 to 20% and for the period for which it is 50 to 80%, the X rays are set to the pulse width for low-speed longer than the standard pulse width. For periods other than those, X rays are set to the standard pulse width shorter than the pulse width for low-speed. The pulse width is dynamically changed according to the heart rate phase, but the frame rate is also changed dynamically together with the pulse width.

The present invention is not limited to the embodiment, and the components can be modified to be embodied without departing from the gist. Further, a plurality of components disclosed in the embodiment is suitably combined so that various inventions can be formed. For example, some components may be deleted from the entire components in the embodiment. Further, components in different embodiments may be suitably combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
   an X-ray generating unit which generates X rays;
   an X-ray detecting unit which detects the X rays transmitted through a subject; and
   a control unit which controls the X-ray generating unit in order to change a pulse width of the X rays according to heart rates of the subject.

2. An X-ray diagnostic apparatus, comprising:
   an X-ray generating unit which generates X rays;
   an X-ray detecting unit which detects the X rays transmitted through a subject; and
   a control unit which controls the X-ray generating unit in order to change at least one of a pulse width and a frame rate of the X rays according to a heart rate phase of the subject.

3. The X-ray diagnostic apparatus according to claim 2, wherein the control unit alternates the pulse width of the X rays between a first pulse width and a second pulse width longer than the first pulse width according to the heart rate phase of the subject.

4. The X-ray diagnostic apparatus according to claim 3, wherein the control unit sets the pulse width of the X rays to the second pulse width for predetermined phase periods.

5. An X-ray diagnostic apparatus, comprising:
   an X-ray generating unit which generates X rays;
   an X-ray detecting unit which detects the X rays transmitted through a subject; and
   a control unit which controls the X-ray generating unit in order to change at least one of a pulse width and a frame rate of the X rays according to heart rates of the subject or a heart rate phase.

* * * * *